United States Patent [19]
Smith et al.

[11] Patent Number: 5,835,200
[45] Date of Patent: Nov. 10, 1998

[54] METHOD AND APPARATUS FOR EXAMINING AN OBJECT

[75] Inventors: Martin Phillip Smith, Berkshire; Robin Wynclyffe Smith, Croydon; Christopher Mark Welbourn, Maidenhead, all of Great Britain

[73] Assignee: Gersan Establishment, Liechtenstein

[21] Appl. No.: 792,058

[22] Filed: Feb. 3, 1997

Related U.S. Application Data

[63] Continuation of Ser. No. 941,097, Dec. 21, 1992, abandoned.

[30] Foreign Application Priority Data

Apr. 24, 1990 [GB] United Kingdom ............... 9009132

[51] Int. Cl.⁶ .................... G01N 21/31; G01N 21/87; G01N 21/65; B07C 5/342
[52] U.S. Cl. .................................................... 356/30
[58] Field of Search ............... 356/30, 418, 419, 356/320

[56] References Cited

U.S. PATENT DOCUMENTS

| | | | |
|---|---|---|---|
| 2,941,444 | 6/1960 | Frykman | 356/419 |
| 3,064,136 | 11/1962 | Mann . | |
| 3,610,756 | 10/1971 | Lenzen et al. . | |
| 3,776,642 | 12/1973 | Anson et al. | 356/188 |
| 3,794,424 | 2/1974 | Eickhorst et al. . | |
| 3,794,425 | 2/1974 | Smith et al. . | |
| 3,828,173 | 8/1974 | Knepler | 235/151.35 |
| 3,833,304 | 9/1974 | Liston | 356/418 |
| 3,861,788 | 1/1975 | Webster | 350/315 |
| 3,999,854 | 12/1976 | Barrett . | |
| 4,081,215 | 3/1978 | Penney et al. . | |
| 4,191,474 | 3/1980 | Passereau | 356/305 |
| 4,259,011 | 3/1981 | Crumm et al. . | |
| 4,286,327 | 8/1981 | Rosenthal et al. | 364/498 |
| 4,291,975 | 9/1981 | Raccah . | |
| 4,394,580 | 7/1983 | Gielisse | 356/30 |
| 4,397,556 | 8/1983 | Müller . | |
| 4,482,245 | 11/1984 | Makabe et al. . | |
| 4,627,008 | 12/1986 | Rosenthal | 364/550 |
| 4,693,377 | 9/1987 | Gerrard et al. . | |
| 4,875,771 | 10/1989 | Bowley et al. . | |
| 4,907,875 | 3/1990 | Bowley et al. . | |

FOREIGN PATENT DOCUMENTS

| | | | |
|---|---|---|---|
| 82302210 | 11/1982 | European Pat. Off. . | |
| 86106509 | 11/1986 | European Pat. Off. . | |
| 89304642 | 12/1989 | European Pat. Off. . | |
| 89305650 | 12/1989 | European Pat. Off. . | |
| A-0358830 | 3/1990 | European Pat. Off. . | |
| A-2 571 144 | 4/1986 | France . | |
| 59691 | 7/1982 | Israel . | |
| TW 098 947 | of 0000 | Japan . | |
| 55-138621 | 10/1980 | Japan . | |
| 57-101709 | 6/1982 | Japan . | |
| 57-108740 | 6/1982 | Japan . | |
| 57-144446 | 9/1982 | Japan . | |
| 57-204440 (A) | 12/1982 | Japan . | |
| 58-728 (A) | 1/1983 | Japan . | |
| PCT/GB89/01532 | 6/1990 | Japan . | |
| 62-22034 | 1/1997 | Japan . | |
| 1050561 | 12/1966 | United Kingdom | 356/419 |
| 1 416 568 | 12/1975 | United Kingdom . | |
| 2 010 474 | 6/1979 | United Kingdom . | |
| 1 595 785 | 8/1981 | United Kingdom . | |
| 2 087 553 | 5/1982 | United Kingdom . | |
| 2 119 509 | 11/1983 | United Kingdom . | |
| 2 151 018 | 7/1985 | United Kingdom . | |
| PCT/GB86/00340 | 12/1986 | United Kingdom . | |
| PCT/GB86/00784 | 7/1987 | United Kingdom . | |
| PCT/GB88/00188 | 8/1988 | United Kingdom . | |
| 2 215 041 | 9/1989 | United Kingdom . | |
| 2 236 848 | 4/1991 | United Kingdom . | |
| PCT/US82/01000 | 3/1983 | WIPO . | |

OTHER PUBLICATIONS

*Applied Optics*, vol. II, No. 7, Jul. 1972, pp. 1637–1638., "Compensation . . ." by M.V.R.K. Murty.

*Opto Spectrosc* (USSR) 46(6), Jun. 1979 pp. 672–675 by G.P. Startsev and A.V. Savushkin.

"Raman Microprobe and Microscope with Laser Excitation", M. Delhaye and P. Dhamel InCourt, pp. 33–43, Journal of Raman Spectroscopy 3 (1975), D. Reidel Publishing Company (no month).

"Laser Raman Spectrometer for Process Control", Arieh M. Karger, Richard P. English, and Ray J.D. Smith, pp. 2083–2087, Sep. 1973, vol.12 No. 9, Applied Optics.

"Optical Determination of Crystal Axis Orientation in Silicon Fragments or Devices", J.J. Gajda and C.D. Needham, pp. 3865–3866, vol. 27 No. 7A, Dec. 1984, IBM Technical Disclosure Bulletin.

"Imagining biological compounds using the coherent anti-–Stokes Raman scattering microscope", M.D. Duncan, J. Reintjes, T.J. Manuccla, pp. 352–355, Mar./Apr. 1985, vol. 24 No. 2, Optical Engineering.

"Multichannel Raman Spectroscopy with a Cooled CCD Imaging Detector", D.N. Batchelder, pp. 28, 32–33, ESN–European Spectroacopy News (1988). (No month).

"Crystalline Colloidal Bragg Diffraction Devices: the Basis for a New Generation of Raman Instrumentation", Sanford A. Asher and Perry L. Flaugh, Guy Washinger, pp. 26–31, Spectroscopy, vol. 1 No. 12 (no date).

"Gem Testing" Anderson & Jobbins. Butterworths, 10th Ed. 1990 pp. 96–97, 124–125, 202–205. (no month).

"Raman Spectroscopy applications of an imaging photomultiplier tube", D. Kirk Veir, Victor K. F. Chia, Gerd M. Rosenblatt, pp. 3530–3534, vol. 26, No. 17, 1 Sep. 1987, Applied Optics.

"Derivative Spectroscopy in the Analysis of Gases", Robert N. Hager and Richard Staodner, pp. 329–364, Technisches Messen, 43 Jahrgard, 1976, Heft II (no month).

Abstract, JP 57–144446, Apparatus for Spectrochemical Analysis.

Abstract, JP 62–22034, Interference Filter Spectral Device.

*Primary Examiner*—Richard A. Rosenberger
*Attorney, Agent, or Firm*—Ostrolenk, Faber, Gerb & Soffen, LLP

[57] ABSTRACT

In order to examine a gemstone, the stone is irradiated and observed though a filter (5) at a first wavelength which is characteristic of a first class of gemstones. The filter can be rocked from a setting normal to the optical axis to transmit radiation of at least one reference wavelength. The intensities of radiation transmitted at first and reference wavelengths are observed and compared, to classify the gemstone as belonging to the first class or not. In order to detect whether the gemstone is a diamond or diamond simulant, the first wavelength comprises raman emission characteristic of diamond. In order to detect whether the gemstone is definitely natural or not definitely natural, the gemstone is classified as definitely natural if there is a maximum of absorption of radiation at 415.5 nm.

29 Claims, 7 Drawing Sheets

FIG. 8

METHOD AND APPARATUS FOR EXAMINING AN OBJECT

This application is a continuation of application Ser. No. 07/941,097, filed on Dec. 21, 1992, now abandoned.

BACKGROUND OF THE INVENTION

The invention is concerned with distinguishing natural diamonds from synthetic diamonds.

WO 86/07457 discloses a method for distinguishing diamond from diamond like simulant, by visually detecting the Raman signal emitted from a specimen which is irradiated with suitable exciting radiation. Diamond simulant comprises dense non-diamond material (eg. metal oxides, particularly zirconium dioxide) which has similar refractive properties to diamond. Synthetic diamond comprises diamond material (ie. crystalline carbon) produced by an industrial process.

The technique disclosed by WO 86/07457 is only suitable for distinguishing diamond from diamond-like simulant. All diamonds, natural or synthetic, show the Raman emission when irradiated with suitable exciting irradiation, and cannot be distinguished by this technique.

THE INVENTION

The invention enables diamonds to be examined and classified by operators with little scientific or technical training.

Preferably, the diamond is irradiated with light in the longwave ultraviolet/visible part of the spectrum and the absorption spectrum of the diamond is studied by measuring the intensity of light absorbed by the diamond.

The diamond may be illuminated with a lamp running off a mains electricity supply. A change in the lamp supply voltage can alter the temperature of the emission source of the lamp and thus the spectral distribution of its output energy may vary. Provision should be made to detect this variation so that parameters such as ratios between transmitted wavelengths can be corrected for errors introduced by the spectral variation. By making more than two observations of the absorption spectrum of the object, any spectral shift due to lamp variation can be detected and compensated for.

The absorption (or, equivalently, transmission) spectrum may be observed by measuring the absorption at 415.5 nm and at least two slightly different reference wavelengths, say 410 nm and 418.5 nm. The absorption should be measured at at least three wavelengths very close together, as this will help to clearly identify a characteristic absorption. 415.5 nm is a very strong absorption, characteristic of diamonds of type IaAB. 418.5 nm and 410 nm fall outside the absorption peak for this characteristic absorption and so the absorption is relatively low. In general, diamonds of different types to IaAB do not show a very strong absorption at 415.5 nm, and even if there is some absorption, it will not be very much different from the absorption at 410 nm and 418.5 nm.

Accordingly, diamonds of type IaAB can be positively distinguished, and as diamonds of this class of diamonds are effectively always natural in origin, the invention allows all diamonds encountered to be classified as belonging to a class consisting of definitely natural diamonds or a class consisting of diamonds which may or may not be natural. This will be explained further below.

The apparatus may be very simple to use and construct, as it only has a small number of components. The whole apparatus may only occupy a space of about 25×10×15 cm, being suitable for use on a bench top. The method does not require any great skill on the part of the operator and is suitable for producing an answer very quickly.

THE DRAWINGS

The invention will be further described by way of example, with reference to the accompanying drawings, in which.

Figure 1:
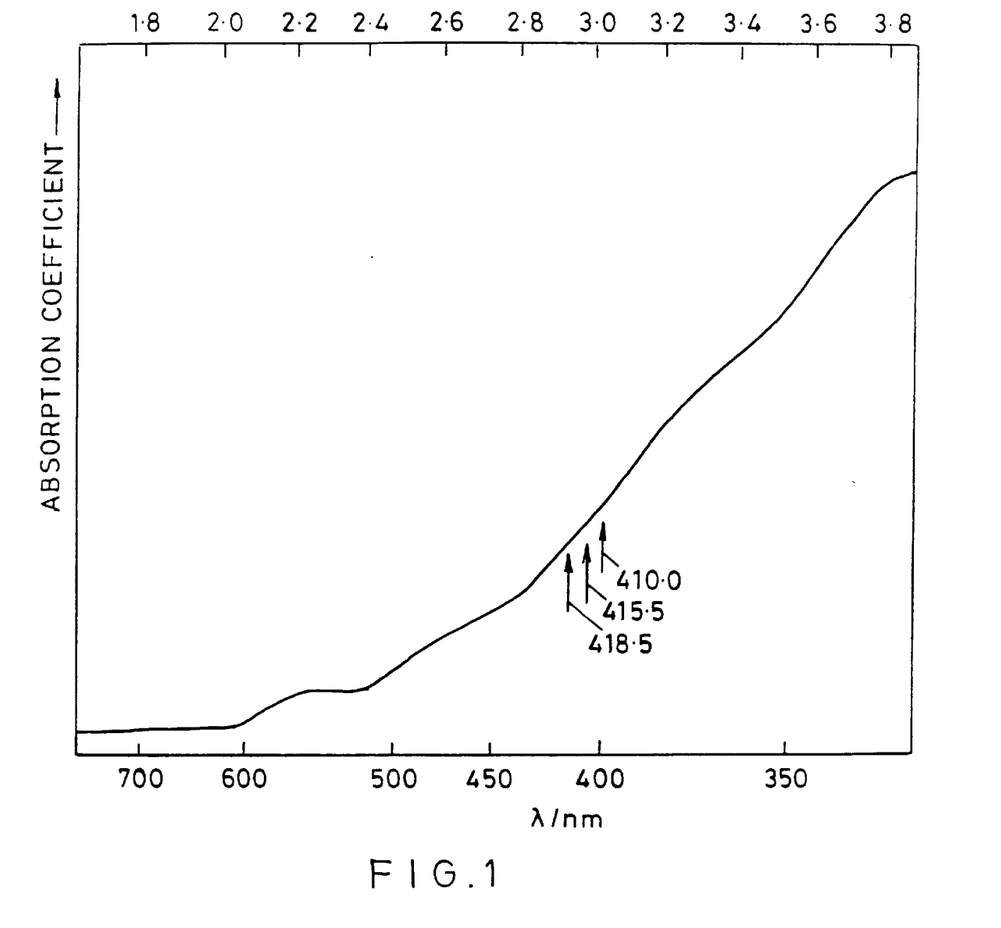
FIG. 1 shows an example of a portion of the absorption spectrum of type Ib diamond.
Figure 2:
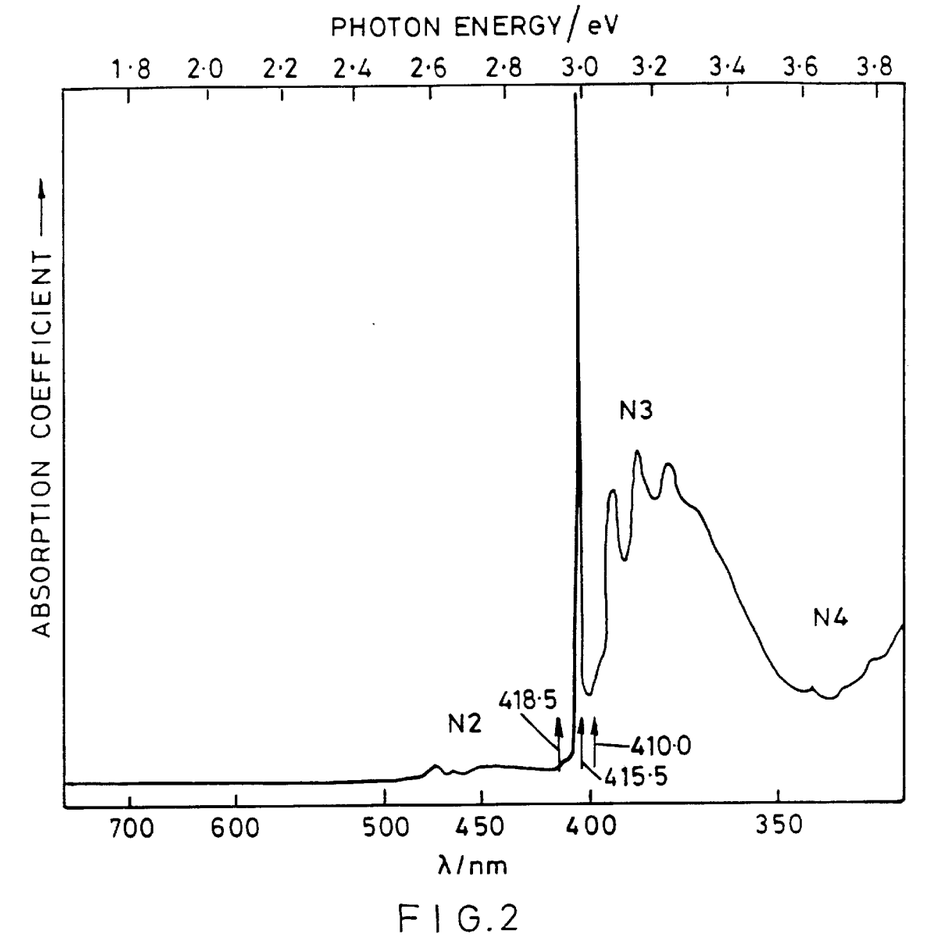
FIG. 2 shows an example of a portion of the absorption spectrum of type IaAB diamonds.
Figure 3:
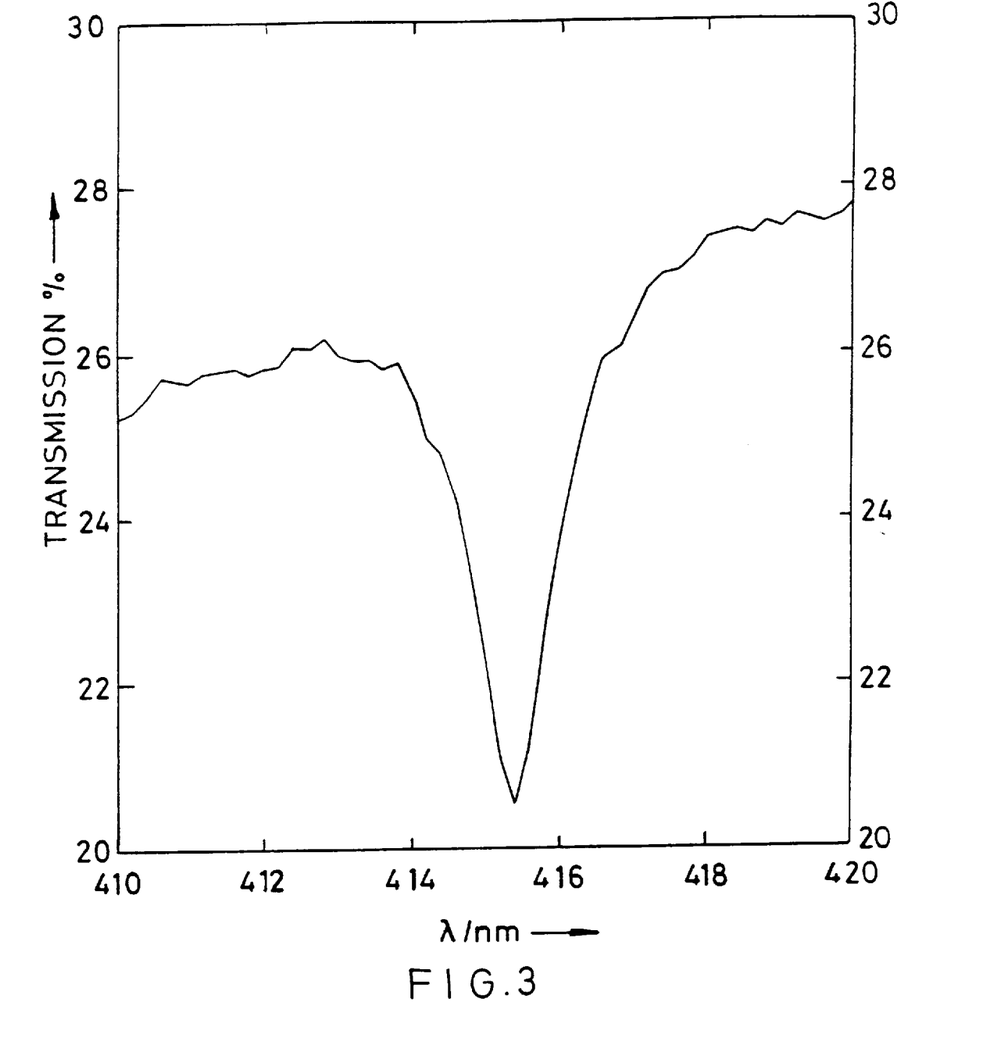
FIG. 3 shows a high resolution transmission spectrum for a type IaAB diamond, between 410 nm and 420 nm.

FIGS. 1 to 3

One way of classifying diamonds is according to their spectroscopic properties. The absorption spectrum of a diamond in the visible region will determine its colour. To a certain extent, it is possible to associate each type of diamond with a range of structure, concentration and composition of impurity defects. An analysis of diamonds in this manner gives the following classification.

Type I

This general type class is defined as the class of diamonds which have a measurable defect induced infra-red absorption in the 1-phonon region (below 1332 cm$^{-1}$). The defects result from the incorporation of nitrogen atoms into the crystal lattice substituting for carbon atoms during growth of the diamond. Natural type I diamonds will typically contain several hundred to a few thousand ppm of nitrogen. The content of nitrogen in synthetic diamonds can be controlled during the process of synthesising the diamonds. This gives a range of nitrogen atom content of a few hundred ppm to practically zero in synthetic diamonds.

The general class type I is divided into the following subtypes:

Type Ib

In this type of diamond single nitrogen atoms are substituted for single carbon atoms at random throughout the lattice. This gives rise to an optical absorption starting at about 600 nm which continues with increasing strength into the longwave ultra-violet region (FIG. 1). This gives rise to the so-called canary yellow colour shown by some diamonds. Type Ib diamonds represent a non-equilibrated form of diamond. Diamonds are formed at conditions of very high temperature and pressure, and if the diamond is maintained at these conditions impurity nitrogen atoms will tend to aggregate. Natural diamonds were usually maintained at these equilibrating conditions for geologically significant periods of time and accordingly type Ib diamonds are rare in nature (much less than 1% of all natural diamonds). On the other hand, synthetic diamonds are not maintained at equilibrating conditions and accordingly most synthetic diamonds are type Ib.

Type Ia

This class comprises diamonds in which the nitrogen has migrated to form more complex defects. There are two principal forms of nitrogen defect which are found in type Ia diamonds, the A form and the B form. The A form comprises pairs of nitrogen atoms on nearest-neighbour substitutional sites. The B form of nitrogen is believed to comprise a complex of four substitutional nitrogen atoms surrounding a vacancy. The ratio of the concentration of A type defects to B type defects varies continuously, the extreme ends of the sequence being labelled type IaA and type IaB. Pure type IaB diamonds are very rare. Synthetic type Ib diamonds can be converted to type IaA by a high-temperature and high-pressure treatment.

Type IaA diamonds have no absorption in the visible region of the spectrum so they are colourless. There is very little visible absorption associated with B centres, and as a result IaB diamonds are colourless. Most natural diamonds contain both A and B centres and are known as type IaAB. In addition to the two principle forms of nitrogen defect, they contain two "by-products" of the nitrogen aggregation process: platelets and N3 centres. Platelets are interstitial planar defects, a few tens of nanometres in diameter lying on cube planes. These give rise to a peak in the infra-red spectrum. N3 centres comprise three co-planar nitrogen atoms probably surrounding a vacancy. N3 centres give rise to absorption between 490 nm and 350 nm with a sharp zero-phonon line at 415.5 nm. This absorption in the blue/violet region causes the so-called cape yellow colour exhibited to a greater or lesser extent by the vast majority of natural diamonds (FIG. 2). FIG. 3 is a high resolution transmission spectrum showing the 415.5 nm absorption of a type IaAB diamond in more detail. It can be seen that there is a strong decrease in transmission at about 415.5 nm, transmission being much higher at other wavelengths, for example 410 nm.

Type IIa

This class comprises diamond in which nitrogen is only present in trace amounts, of the order of 1 ppm. There is often a form of background absorption at the shorter wavelength end of the visible spectrum, giving some of these diamonds a generally brown colour. This near absence of nitrogen in diamonds rarely occurs in nature (less than 2% of natural diamonds are type IIa) but can be assurred in the production of synthetic diamonds.

Type IIb

This is a very rare class of semiconducting diamonds in nature. The diamonds contain trace amounts of substitutional boron as semiconductor acceptor centres which give the diamonds a bluish colour due to the tail of the photoionization spectrum at the acceptor centre. Type IIb diamonds are generally natural, but synthetic diamonds containing added boron can be produced.

In all, most natural diamonds are type IaAB and IaA, only about 2% being II, Ib or IaB.

Figure 4:
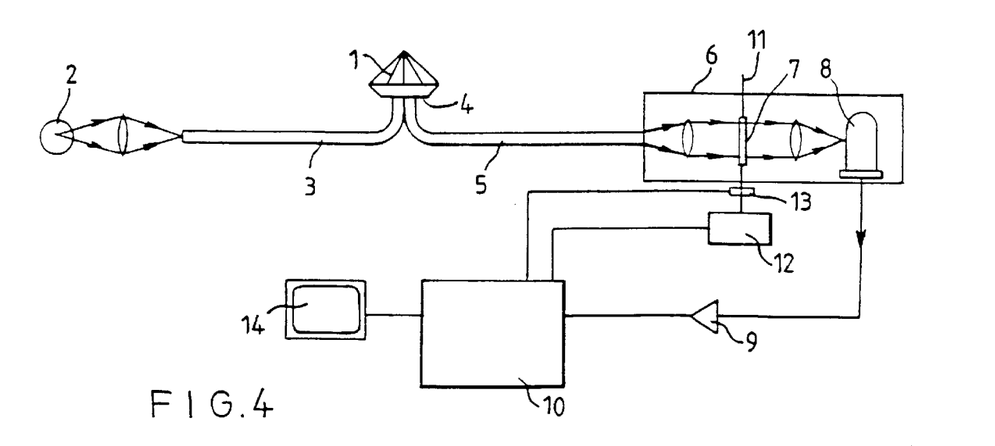
FIG. 4 shows an apparatus for observing a diamond according to the invention.

FIG. 4

FIG. 4 is a schematic drawing of apparatus according to the invention, which is set up to classify a finished diamond as definitely natural or not definitely natural.

A diamond 1 is illuminated with radiation generated by a halogen lamp 2 of a suitable wavelength. The illuminating radiation is fed to the diamond via a fibre optic 3 and, in the case of a brilliant cut diamond, the light is fed in through the table of the diamond. A brilliant cut diamond is intended to be viewed through the table and is so shaped that the maximum amount of light is reflected by the lower faces of the diamond back out of the table 4. In order to study the absorption spectrum of the diamond, a second fibre optic 5 is provided to collect light leaving the diamond via the table 4. Transmitted light is fed via the fibre optic 5 into detector apparatus 6 which includes a filter 7. A photomultiplier tube or other photodetector 8 is provided to give a signal dependent upon the intensity of light passed by the filter 7, which signal is fed to an amplifier 9 and then to a microprocessor 10. The filter 7 is rotatable about an axis 11 to transmit light at different wavelengths. Rotation can be driven by a motor 12 or by hand. The motor 12 can be controlled by the microprocessor 10, a transducer 13 comprising a shaft encoder or the like being provided to give a signal indicating the position of the filter 7. In order for the readings taken by the apparatus to be simply presented and easily understood, a visual display unit (VDU) 14 may be provided receiving signals from the microprocessor 10.

Figure 5:
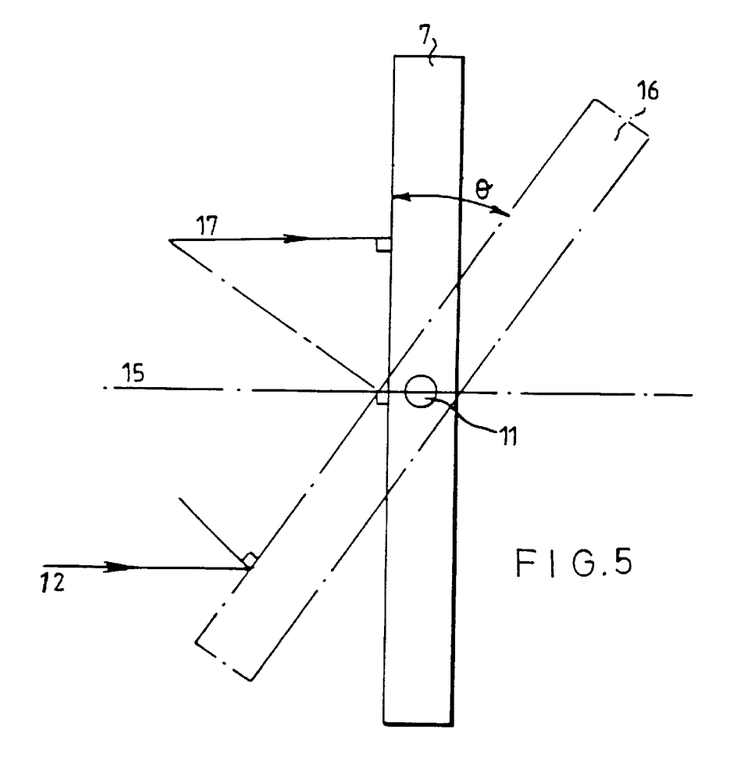
FIG. 5 shows the filter of the apparatus of FIG. 4 in first and second positions.
Figure 6:
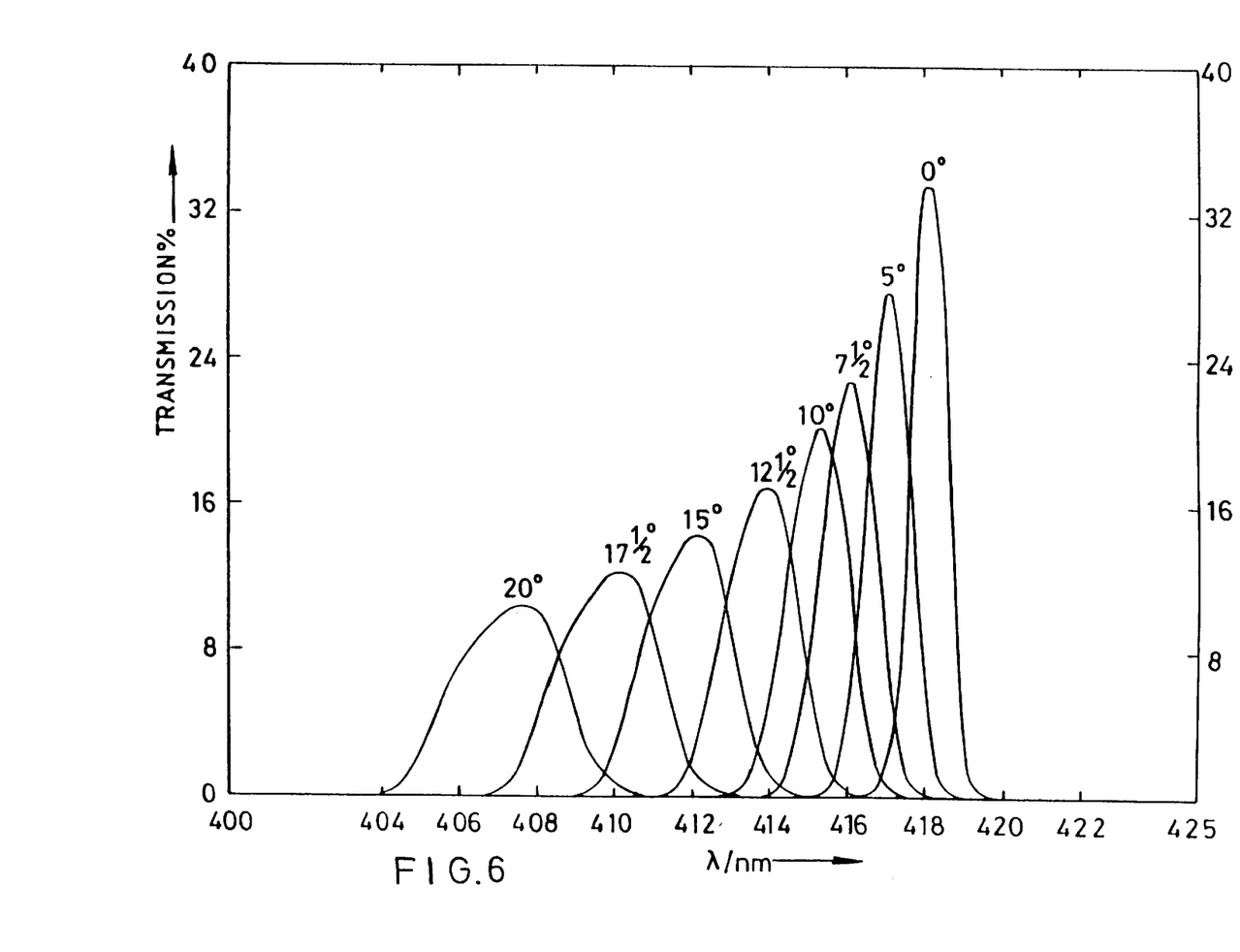
FIG. 6 shows the variation with angle of incidence of band pass characteristics of the filter of FIGS. 4 and 5.

As shown in FIG. 5, the filter 7 can be rotated about an axis 11 normal to its optical axis 15 into a tilted position (as shown at 16). The band pass characteristics of the filter 7 vary with the angle θ between the optical axis 15 of the filter and the direction of incident light 17. FIG. 6 shows the band pass characteristics of a CWL=418.5 nm filter at various values of θ. It may be seen that as θ increases, the maximum of the transmission moves to lower wavelength, the transmission maximum decreases in intensity and the width of the band passed increases. The full width at half maximum for the filter where θ=0 is 1 nm. Such a filter is manufactured by Omega Optical Company in the U.S.A.

Thus, if the filter 7 is tilted through a variety of angles θ by the motor 12, a region of the absorption spectrum of the diamond 1 may be scanned and sampled.

The apparatus shown in FIG. 4 can be used to classify a diamond as belonging to type IaAB or not. A filter 7 having the band pass characteristic shown in FIG. 6 is used, so that a signal can be derived representive of the absorption of light at 415.5 nm. On its own, this signal does not give much useful information unless it is normalized, because the signal will vary with the size of the diamond. Furthermore, diamonds of type IaAB will vary greatly in the absorption co-efficient at 415.5 nm between themselves, and no positive range can be assigned to clearly identify a diamond of type IaAB on the basis of this one uncorrected absorption signal alone. Accordingly, a second measurement is taken at a reference wavelength of 410 nm for example. This lies substantially outside the absorption peak 415.5 nm and is of higher energy. In general, for non type IaAB diamonds measurements at 415.5 nm and 410 nm would be expected to be very similar in size, the absorption at higher wavelength being lower if there were any difference. In the case of diamonds of type IaAB, the absorption at longer wavelength is expected to be much stronger.

The lamp 2 used to illuminate the diamond may be an halogen lamp, for example a 12 volt, 12 watt Thorn type M64 with a Spindler and Hoyer lens 063097. This form of lamp operates at about 3,000K with a peak at the red end of the visible spectrum. The wavelengths to be observed lie on a steep part of the thermal radiation curve. Accordingly, if the temperature of the lamp shifts to, say, 3,200K due to a perturbation in the power supply, the shape of the curve will vary and the intensity of light at the wavelengths to be observed will vary quite markedly, the ratio of the intensities between the two irradiating wavelengths will vary, and so the reading based upon the intensity of radiation absorbed at these wavelengths by the diamond can be in error. In order to detect this error, a third measurement may be made at a wavelength of, for example 418.5 nm. Preferably, a series of measurements are made in the region 418.5 to 410 nm, and the absorption results interpreted by a curve fitting technique, operated by the microprocessor 10 to detect if a 415.5 nm absorption is in fact present.

The filter 7 may be rotated at high speed (3,000 rpm) about its axis 11 and the absorption of light at various wavelengths (deducible from the angle θ of the filter, measured by transducer 13) measured many times over and stored by the microprocessor. A mass of data is obtained quickly and simply which can be analysed by a statistical technique to provide more accurate information on the absorption characteristics of the diamond. This improves the repeatability of the test and reduces the error.

The microprocessor 10 can be programmed to compare the readings directly and to produce a signal representative of whether the diamond is natural or should be tested further, or all the readings may be shown numerically, or graphically on the VDU 14.

Figure 7:
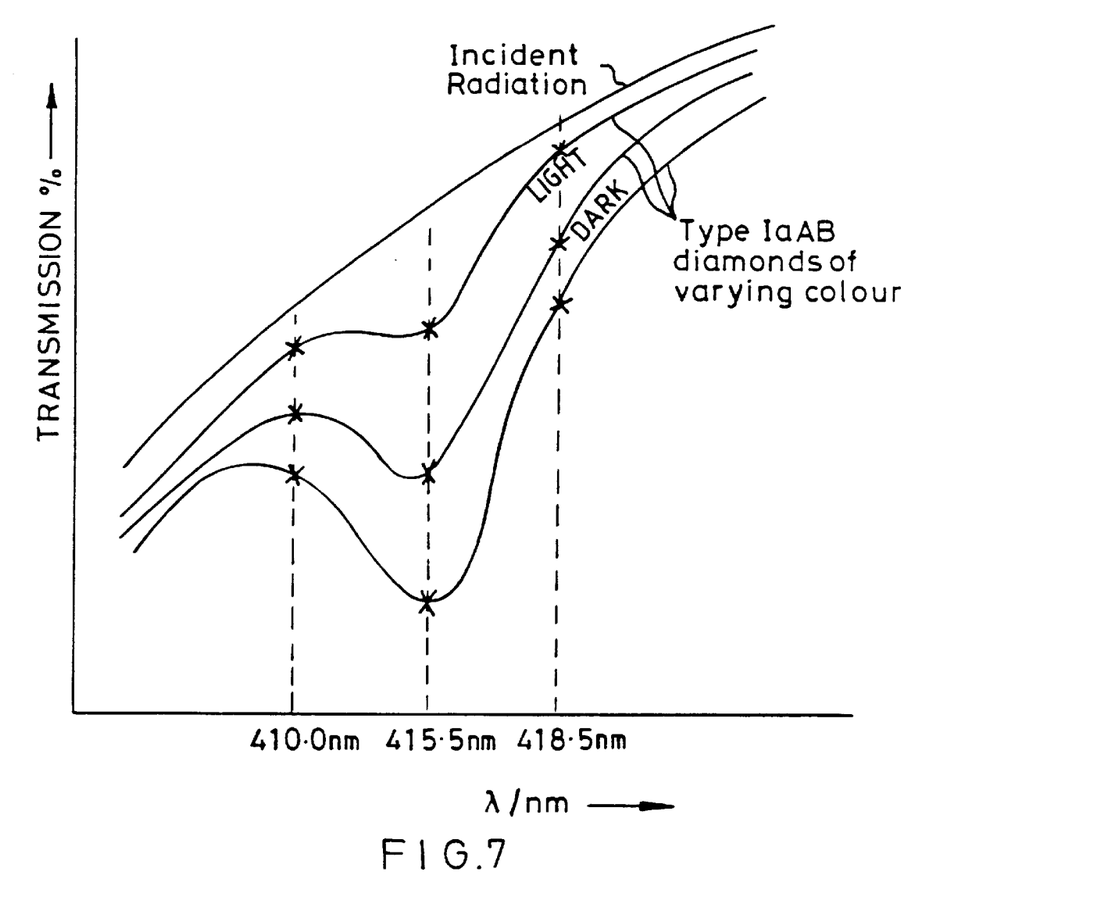
FIG. 7 shows the use of three observations to fit a curve.
Figure 8:
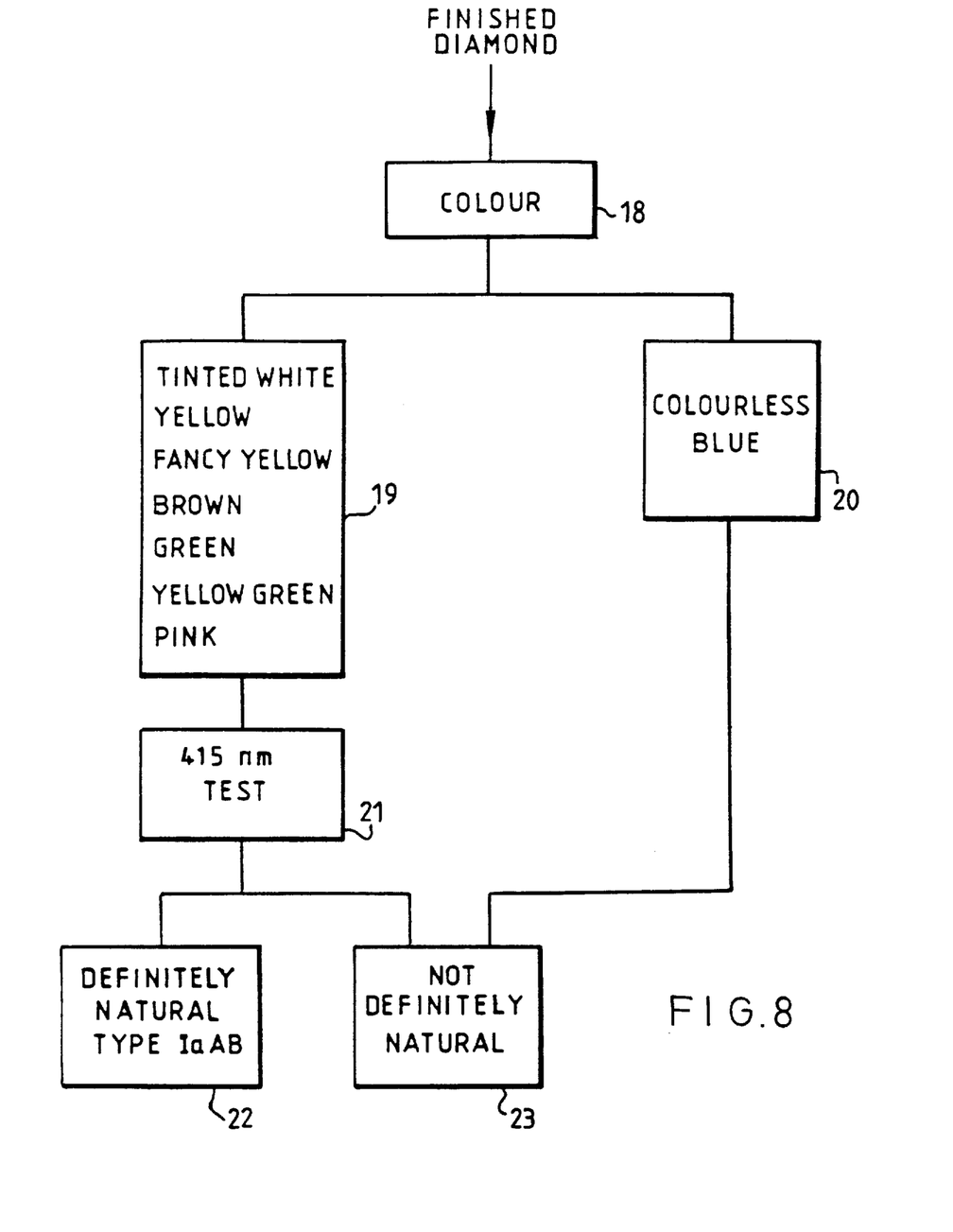
FIG. 8 shows a flow chart for use with the invention.

FIG. 7 shows how the three measurements at 410, 415.5 and 418.5 nm can be used in the microprocessor to plot a curve showing the absorption characteristics of the diamond in this region of the spectrum, so that an absorption at 415.5 nm can be clearly identified.

Three absorption curves are shown, for diamonds of type IaAB showing the cape yellow colour with varying degrees of intensity.

Instead of correcting the first and second wavelength measurements using a third wavelength and a curve fitting technique, the spectrum of the lamp 2 may be sampled directly, using a reference channel. A third fibre optic may be used, leading directly from the lamp 2 to a detector, which passes data to the microprocessor 10.

Being able to classify a diamond as type IaAB or not will be useful to the jeweller or other craftsman in identifying natural diamonds, as the vast majority of natural diamonds belong to class IaAB and (because of the complexity of the defects and the fact that they take a long time to develop) synthetic diamonds are effectively never type IaAB. Thus the apparatus of the invention can be set up as above, to divide all diamonds into one of two classes:

definitely natural;

possibly natural, possibly synthetic;

The number of natural diamonds classified in the second class by the apparatus of FIG. 4 will be very small (about 2%), comprising type Ia, Ib, IIa, IIb and IaA or IaB diamonds, which are all very rare.

The apparatus of FIG. 4 can also be used to measure the colour of a cape diamond, by measuring the strength of the 415.5 nm absorption.

In the apparatus shown in FIG. 4, the lamp 2 may be a 12 volt 12 watt halogen lamp manufactured by Thorn, type M64, using a lens 063097 manufactured by Spindler and Hoyer Limited. Suitable fibre optic cable is manufactured by Schott. The lenses shown in the detector 6 are, from left to right, a lens 063097 and lens 063045 respectively, both manufactured by Spindler and Hoyer. The photomultiplier tube 8 can be of the type manufactured by Hamamatsu KK. FIG. 9

FIG. 9 shows a flow chart for classifying a finished diamond using apparatus according to the first and second aspects of the invention. The diamond is first analysed in terms of its colour at 18. Two classes 19, 20 are produced, consisting of the following colour types (with their estimated occurence, as a percentage, derived from intake figures for +0.5 ct rough diamonds):

Class 1

Tinted white to yellow (72%)

Fancy yellow (less than 0.1%)

Brown (approximately 1%)

Green and yellow green (less than 0.1%)

Pink (less than 0.1%)

Class 2

Colourless (27%)

Blue (less than 0.1%)

Diamonds of Class 1 are subjected to the 415.5 nm test at 21 to produce a class of diamonds which are definitely natural (type IaAB) and a class of diamonds which are not definitely natural or 22 and 23. Class II diamonds are rejected as not definitely natural.

The present invention has been described above purely by way of example, and modifications can be made within the spirit of the invention. The invention also consists in any individual features described or implicit herein or shown or implicit in the drawings or any combination of such features or any generalisation of any such features or combination.

We claim:

1. A method of classifying a diamond as belonging to a first class consisting of definitely natural diamonds or to a class comprising diamonds which may or may not be natural, comprising:

irradiating the diamond;

observing the diamond through a narrow band pass filter that passes radiation of a wavelength corresponding substantially to a characteristic wavelength peak in the absorption spectrum of the first class of diamond;

the diamond being observed by cycling the wavelength passed by the filter a number of times through each wavelength of a set of wavelengths including the characteristic wavelength peak and at least two reference wavelengths in the region of the characteristic wavelength peak;

making a plurality of measurements of the intensity of radiation passing through the filter at each of the wavelengths of said set and storing each of the measurements;

determining whether the characteristic wavelength peak is present or absent in the absorption spectrum of the diamond on the basis of the measurements and thereby classifying the diamond as belonging to the first class or not on the basis of the measurements.

2. The method of claim 1, wherein the filter is tilted about an axis normal to its optical axis to alter the band of radiation passed by the filter.

3. The method of claim 2, wherein the filter is tilted to and from between a first position and a second position.

4. The method of claim 1, wherein the object is irradiated with radiation of a plurality of wavelengths and the intensity of radiation transmitted by the object is observed through the narrow band pass filter.

5. The method of claim 1, wherein the reference wavelengths and the characteristic wavelength are within approximately 15 nm of each other.

6. The method of claim 4, wherein the intensity of radiation transmitted by the object at the first wavelength and at the reference wavelengths is observed, and wherein the reference wavelengths lie outside but adjacent the absorption peak corresponding to the characteristic wavelength in the absorption spectrum of an object of the particular class to show any significant difference within a narrow range of wavelengths.

7. The method of claim 4, wherein the method is for examining diamonds, the characteristic wavelength being substantially equal to 415.5 nm, and the particular class of object comprising type IaAB diamonds.

8. The method of claim 7, wherein one of the reference wavelengths is substantially equal to 410 nm.

9. The method of claim 9, wherein the reference wavelengths and the characteristic wavelength are within approximately 15 nm of each other.

10. The method of claim 1, further comprising using the observation at a first reference wavelength to correct the observations at the characteristic wavelength and at least one second reference wavelength to correct for spectral variations in the radiation irradiating the object.

11. The method of claim 1, wherein the object is observed at a large number of wavelengths, including the first wavelength and the two reference wavelengths.

12. A method of claim 1, wherein the measurements of the radiation transmitted at each of the wavelengths of the set are combined mathematically to provides a combined signal substantially independent of the size of the object, the object being classified as belonging to the particular class of objects or not in response to said combined signal.

13. The method of claim 12, wherein the measurements are combined by a statistical technique.

14. Apparatus for classifying a diamond as belonging to a first class consisting of definitely natural diamonds or to a class comprising diamonds which may or may not be natural, comprising:
means for irradiating the diamond;
a filter which passes radiation at a wavelength corresponding substantially to a characteristic wavelength peak in the absorption spectrum of the first class of diamond;
means for tilting the filter to cyclically alter the band of radiation passed by the filter through each of a set of wavelengths including the characteristic wavelength peak and at least two reference wavelengths different from the characteristic wavelength peak in the region of the characteristic wavelength peak;
means for generating signals dependent upon the intensity of radiation passing through the filter at each of the wavelengths of said set;
means for storing each of said signals; and
means for determining whether the characteristic wavelength peak is present or absent in the absorption spectrum of the diamond on the basis of the signals and thereby classifying the diamond as belonging to the first class or not on the basis of the signals.

15. The apparatus of claim 14, wherein the means for altering the wavelength passed by the filter is for placing the filter in a plurality of positions and the signal generating means is set up to generate a signal dependent upon the intensity of light transmitted by the object at each of said plurality of positions of the filter, said plurality of positions including said first and said two further positions.

16. The apparatus of claim 15, wherein the means for altering the wavelength passed by the filter is for placing the filter in each of said plurality of positions a number of times, the signal generating means being set upon to provide a signal dependent upon the intensity of radiation passing through the filter each time it is in each of said plurality of positions, the resulting signals being input to the computing means.

17. The apparatus of claim 14, wherein the filter is tiltable about an axis normal to its optical axis.

18. The apparatus of claim 14, wherein the irradiating means is for irradiating the object with radiation of a plurality of wavelengths and the apparatus is set up so that signals dependent upon the intensity of radiation transmitted by the object are provided by said signal generating means.

19. The apparatus of claim 14, wherein said reference wavelengths and said characteristic wavelength are within approximately 15 nm of each other.

20. The apparatus of claim 14, wherein the reference wavelengths lie outside but adjacent the absorption peak corresponding to the characteristic wavelength in the absorption spectrum of an object of the particular class to show any significant difference within a narrow range of wavelengths.

21. The apparatus of claim 14, being set up to examine diamonds, the characteristic wavelength being substantially equal to 415.5 nm, and the particular class of object comprising type IaAB diamonds.

22. The apparatus of claim 21, wherein one of the reference wavelength is substantially equal to 410 nm.

23. The apparatus of claim 22, wherein said reference wavelengths and said characteristic wavelength are within approximately 15 nm of each other.

24. The apparatus of claim 14, further comprising computing means which is set up to combine the signals dependent upon the intensity of radiation passing through the filter mathematically, to provide a combined signal substantially independent of the size of the object, the object being classified as belonging to said first class of objects or not in response to said combined signal.

25. The apparatus of claim 24, wherein the computing means is set up to combine the signals statistically.

26. A method of classifying a diamond as belonging to a first class consisting of definitely natural diamonds or to a class comprising diamonds which may or may not be natural, comprising:
irradiating a diamond with radiation of a plurality of wavelengths;
observing through a narrow band pass filter radiation transmitted by the diamond, and altering the band passed by the filter, wherein radiation transmitted is observed at a wavelength corresponding substantially to a characteristic wavelength peak in the absorption spectrum of the first class of diamond and at least one reference wavelength in the region of the characteristic wavelength peak;
the diamond being observed by measuring the intensity of radiation passing through the narrow band pass filter,
making a plurality of measurements of the intensity of radiation transmitted by the object at said characteristic and reference wavelength and storing said measurements over time; and
classifying the diamond as belonging to the first class or not in response to a pattern determined from the measurements stored over time.

27. Apparatus for classifying a diamond as belonging to a first class consisting of definitely natural diamonds or to a class comprising diamonds which may or may not be natural, comprising:
means for irradiating the diamond with radiation of a plurality of wavelengths;
means for generating intensity signals dependent upon the intensity of light transmitted by the diamond at a wavelength corresponding substantially to a characteristic wavelength peak in the absorption spectrum of the first class of diamond and at least one reference wavelength in the region of the characteristic wavelength peak, comprising a narrow band pass filter and means for altering the wavelength passed by the filter, wherein the narrow band pass filter passes radiation of the characteristic wavelength peak in a first position and radiation of the reference wavelength in a second position, the means for altering the wavelength passed by the filter cycling the filter repeatedly between said first position and second position, so that a signal dependent upon the intensity of radiation transmitted by the filter is given each time the filter is in said first or second position; and computing means for storing each of the signals and for combining the signals to provide a combined signal substantially independent of the size of the diamond and for classifying the diamond as belonging to the first class or not on the basis of the combined signal.

28. Apparatus for classifying a diamond as belonging to a first class consisting of definitely natural diamonds or to a class comprising diamonds which may or may not be natural, comprising:

an irradiation source for irradiating the diamond;

a filter which passes radiation at a wavelength substantially corresponding to a characteristic wavelength peak in the absorption spectrum of the first class of diamond;

a drive for tilting the filter to cyclically alter the band of radiation passed by the filter through each of a set of wavelengths including the characteristic wavelength peak and at least two reference wavelengths in the region of the characteristic wavelength peak; and a sensor for generating signals dependent upon the intensity of radiation passing through the filter at each of the wavelengths of said set, and a computer for storing each of said signals each time the filter is cycled through said set and for classifying the diamond as belonging to the first class or not on the basis of a pattern determined from the signals stored over time.

29. A method of classifying a diamond as belonging to a first class consisting of definitely natural diamonds or to a class comprising diamonds which may or may not be natural, comprising:

irradiating the diamond;

observing the diamond through a narrow band pass filter that passes radiation of a wavelength corresponding substantially to a characteristic wavelength peak in the absorption spectrum of the first class of diamond;

the diamond being observed by tilting the filter to cycle the wavelength passed by the filter a number of times through each wavelength of a set of wavelengths including the characteristic wavelength peak and at least two reference wavelengths in the region of the characteristic wavelength peak;

making a measurement of the intensity of the radiation passing through the filter at each of the wavelengths of said set each time the filter is cycled through said set; and storing said measurements;

the measurements at the wavelengths of said set being used to classify the object as belonging to the first class of diamond or not.

* * * * *